United States Patent [19]
Pereira

[11] Patent Number: 6,087,551
[45] Date of Patent: *Jul. 11, 2000

[54] MULTI-DENIER NON-WOVEN FABRIC FOR DISPOSABLE ABSORBENT PRODUCTS

[75] Inventor: Jose Antonio Pereira, Sao Jose dos Campos, Brazil

[73] Assignee: McNeil-PPC, Inc., Skillman, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/780,193

[22] Filed: Jan. 10, 1997

[51] Int. Cl.⁷ ..................................................... A61F 13/15
[52] U.S. Cl. ...................... 604/367; 604/365; 604/385.1; 604/358
[58] Field of Search .................................. 604/365, 367, 604/385.1, 358

[56] References Cited

U.S. PATENT DOCUMENTS

| | | |
|---|---|---|
| 4,077,410 | 3/1978 | Butterworth et al. . |
| 4,216,772 | 8/1980 | Tsuchiya et al. . |
| 4,307,721 | 12/1981 | Tsuchiya et al. . |
| 4,377,615 | 3/1983 | Suzuki et al. . |
| 4,468,428 | 8/1984 | Early et al. . |
| 4,537,822 | 8/1985 | Nanri et al. . |
| 4,728,394 | 3/1988 | Shinjou et al. . |
| 4,801,494 | 1/1989 | Datta et al. ............................... 428/283 |
| 4,810,556 | 3/1989 | Kobayashi et al. . |
| 4,868,031 | 9/1989 | Modrak et al. . |
| 4,892,534 | 1/1990 | Datta et al. . |
| 5,133,835 | 7/1992 | Goettmann et al. . |
| 5,171,238 | 12/1992 | Kajander . |
| 5,204,165 | 4/1993 | Schortmann . |
| 5,257,982 | 11/1993 | Cohen et al. . |
| 5,271,780 | 12/1993 | Baigas, Jr. . |
| 5,403,444 | 4/1995 | Goettmann et al. . |
| 5,433,715 | 7/1995 | Tanzer et al. ............................ 604/368 |
| 5,437,653 | 8/1995 | Gilman et al. . |
| 5,486,166 | 1/1996 | Bishop et al. . |
| 5,490,846 | 2/1996 | Ellis et al. ............................... 604/366 |
| 5,509,915 | 4/1996 | Hanson et al. .......................... 604/378 |

*Primary Examiner*—John G. Weiss
*Assistant Examiner*—Miley Craig Peppers, III
*Attorney, Agent, or Firm*—James P. Barr

[57] ABSTRACT

A multi-denier non-woven fabric suitable for use as a body side liner in disposable absorbent products such as diapers, sanitary napkins, underpads, surgical dressings, tampons, and the like. The multi-denier non-woven fabric is made from an interconnected network thermoplastic polymer fiber elements comprising a homogeneous blend of high denier and low denier fibers having a denier in a range of from 2 to 15 denier, wherein the high denier fiber elements and the low denier fiber elements differ by at least one denier.

18 Claims, No Drawings

MULTI-DENIER NON-WOVEN FABRIC FOR DISPOSABLE ABSORBENT PRODUCTS

FIELD OF THE INVENTION

This invention relates to a novel non-woven fabric suitable for use as a body side liner in disposable absorbent products such as sanitary napkins, surgical dressings, tampons, and the like, and more particularly to a multi-denier non-woven fabric made from an interconnected network thermoplastic polymer fibers comprising a homogeneous blend of high denier staple fibers and low denier staple fibers.

BACKGROUND OF THE INVENTION

Non-woven, bonded, textile/pulp fabrics, hydraulically entangled, thermally bonded, chemically bonded and mechanically-bonded textile fiber fabrics, and relatively thin, spun-bonded fabrics are commonly used facing fabrics for disposable sanitary and convenience products. Such fabrics should be relatively soft and conformable, capable of extended contact with external and internal body surfaces without causing chafing or allergenic reactions, and also capable of transmitting body fluids to a central absorbent core while maintaining skin dryness.

Because of the desire to provide disposable sanitary absorbent articles with body facing materials which are clean and dry, these products use synthetic fibers such as polypropylene, polyethylene, polyester and the like. Non-woven fabric covers derived from synthetic fibers having a denier of 3 or less have generally been used as body-facing covers for disposable sanitary absorbent articles. However, these non-woven fabrics have not been found to adequately provide body facing materials for absorbent articles which rapidly absorb menstrual fluids, mask absorbed fluids, provide a dry surface to the wearer and have the desired softness.

SUMMARY OF THE INVENTION

It is an object of the present invention to provide a novel non-woven fabric which is useful as a body-side liner for absorbent articles.

It is another object of this invention to provide a novel non-woven fabric which is capable of rapidly acquiring fluid with limited retention and which is capable of masking absorbed fluids.

It is another object of this invention to provide an absorbent article which utilizes a multi-denier non-woven fabric as a body side liner.

In accordance with the present invention, there has been provided a novel multi-denier non-woven fabric formed from an interconnected network thermoplastic polymer staple fibers, the fibers comprising a homogeneous blend of high denier staple fibers and low denier staple fibers having a denier in a range of from 2 denier to 15 denier, wherein the high denier staple fibers and the low denier staple fibers differ by at least one denier and wherein the high denier staple fibers are present in the blend in an amount of from 10 to 90% and the low denier staple fibers are present in the blend in an amount of from 90 to 10%.

Also provided in accordance with the present invention, is a novel absorbent article having a body-facing fluid permeable cover sheet comprising a multi-denier non-woven fabric formed from an interconnected network thermoplastic polymer staple fibers, the fibers comprising a homogeneous blend of high denier fibers and low denier fibers having a denier in a range of from 2 denier to 15 denier, wherein the high denier fibers and the low denier fibers differ by at least one denier and wherein the high denier fibers are present in the blend in an amount of from 10 to 90% and the low denier fibers are present in the blend in an amount of from 90 to 10%.

Also provided in accordance with the present invention, is a novel absorbent article such as a sanitary napkin having a body-facing fluid permeable cover sheet, a garment-facing fluid impermeable barrier sheet, an absorbent core between the cover sheet and the barrier sheet, wherein the cover sheet is a non-woven fabric formed from an interconnected network thermoplastic polymer fibers, the fibers comprising a homogeneous blend of high denier fibers and low denier fibers having a denier in a range of from 2 denier to 15 denier, wherein the high denier fibers and the low denier fibers differ by at least one denier and wherein the high denier fibers are present in the blend in an amount of from 10 to 90% and the low denier fibers are present in the blend in an amount of from 90 to 10%.

The absorbent articles of this invention absorb body fluids and are useful as body-side liners in disposable diapers, sanitary napkins, tampons, underpads, surgical dressings and wipes. The absorbent articles can be used as separate entities, or can be integral parts of a disposable or a limited use garment.

DESCRIPTION OF PREFERRED EMBODIMENTS

The present invention is directed to a novel multi-denier non-woven fabric formed from an interconnected network thermoplastic polymer staple fibers. More specifically, the fabric is formed from a homogeneous blend of high denier staple fibers and low denier staple fibers having a denier in a range of from 2 denier to 15 denier and preferably have a denier in the range of from 3 denier to 6 denier. It is considered an important feature of the present invention that the high denier staple fibers and the low denier staple fibers differ by at least one denier, and preferably differ by 2 denier. In a preferred embodiment, the low denier staple fibers have a denier of from about 2 to 4 and most preferably have a denier of about 3 and the high denier staple fibers have a denier of from about 4 to 15 and most preferably have a denier of about 5. The high denier staple fibers are present in the non-woven fabric in an amount of from 10 to 90 weight percent, preferably in a range of from 30 to 70 weight percent, and most preferably in a range of from 40 to 60 weight percent. The low denier staple fibers are present in the non-woven fabric in an amount of from 90 to 10 weight percent, preferably in a range of from 30 to 70 weight percent, and most preferably in a range of from 40 to 60 weight percent based on the total weight of the non-woven fabric.

Suitable fibers for use in the present invention include, but are not limited to, synthetic polymeric fibers formed from thermoplastic resins such as polypropylene, polyester, polyethylene, polyacrylate, and the like and combinations thereof. A preferred synthetic polymeric fiber is polypropylene. As noted above, the fibers used to form the non-woven fabric of the present invention are staple fibers, and generally have a fiber length in a range of from 1 inch to 4 inches, and preferably have a fiber length in the range of from 1.25 inches to 3 inches.

The non-woven fabrics of the present invention may be formed by conventional processes including thermobonding, resin bonding, and spunlacing processes. In all of these manufacturing processes, the initial process step is to form a web of homogeneously mixed low and high denier fibers. Accordingly, bales of low denier staple fibers and high denier staple fibers are homogeneously mixed in an air mixing chamber and then either carded to form a carded web or randomly laid on a foraminous forming structure to form a fibrous web. When utilizing a thermobonding process, the web of homogeneously mixed low denier and high denier fibers may be fed into a calendering station equipped with a heated flat anvil roll and a patterned embossing roll which bonds the fibers and stabilizes the web into a non-woven fabric. An alternative thermobonding process involves forcing heated air through the web and is generally known as a through-air bonding process. In a resin bonding process, the web of homogeneously mixed low denier and high denier fibers is formed as above and passed through a forming drum equipped with a series of water spray nozzles (i.e. having a pressure of about 200 psi) which are capable of lightly entangling the fibers. The entangled web is then de-watered and fed into a binder printing station where the fabric is impregnated with a binder. The binder-impregnated fabric is then dried and cured in an oven. Alternatively, the fibrous web may be sprayed with resin powders under vacuum and then through-air bonded in an oven. Finally, in a spunlace process, the homogeneous blend of low and high denier staple fibers is passed through a series of high pressure water jets, i.e. having a pressure of from 500 to 1500 psi. to highly entangle the fiber web into a stabilized fabric. The fabric is then de-watered and dried. All of the foregoing processes are well known to those of ordinary skill in the art and the choice of one process over another process is not, per se, critical to the invention, provided of course that the resultant non-woven fabric has sufficient structural integrity to permit it to be adapted as a cover material for absorbent articles. In general, a non-woven fabric has sufficient structural integrity when the tensile strength is about one pound per inch. Sufficient structural integrity is achieved when the bonding area comprises from 10 to 40 percent of the total fabric area, and is preferably in a range of from 15 to 20 percent of the total fabric area. It is preferred that the non-woven fabrics of the present invention be a carded web formed by a thermobonding process utilizing hot patterned calender rolls.

The ability of a non-woven fabric to mask absorbed fluids, particularly menstrual fluid, is an important consideration in the development of body-side liners for absorbent articles. Accordingly, the fibers of the present invention are preferably provided with a colorant. A preferred color is a white color, preferably formed by titanium dioxide. The titanium dioxide content of the fibers is present in an amount to provide sufficient opacity to the fiber and thereby provide good masking of absorbed fluids. The titanium dioxide content is preferably between about 1 to 6 weight percent, and is most preferably in a range of from 2 to 2.5 weight percent. An alternative colorant is calcium carbonate, and is present in a range of from 50 to 20 weight percent. Mixtures of calcium carbonate and titanium dioxide may also be used.

When the multi-denier non-woven fabrics are utilized as body-side liners in disposable absorbent articles, it is generally desirable that the body side liner have a durable hydrophilic finish so that the portion of the absorbent article in contact with a wearer's skin remains hydrophilic after multiple fluid introductions. Hydrophilic finishes provide enhanced body fluid transport away from the wearer which aids in transporting the body fluids to the underlying absorbent core. The fibers of the present invention may be treated with a durable hydrophilic surface active agent, such as, for example, a nonionic surfactant which is commercially available under the tradename ATMER from ICI Polymer Additives, New Castle, Del. Other suitable hydrophilic surface active agents include, but are not limited to sodium salts of dioctyl sulfosuccinate (commercially available under the designation AEROSOL OT), non-ionic polyoxy-ethylene sorbitan monolaurate (commercially available under the designation TWEEN 20), or the like. The durable hydrophilic finish may be applied to the fiber surface by dipping fibers into an aqueous solution of the desired surface active agent or by spraying an aqueous solution of the desired surface active agent onto outer surface and subsequently drying the fibers. The surface active agent may be deposited on the non-woven fabric by means of a roller which has been wetted with an aqueous solution of the surface active agent which is passed over inner surface of non-woven fabric so as to deposit the surface active agent near and on an inner surface while the outer surface retains a substantially hydrophobic character. Alternatively, internal hydrophilic surfactants or wetting agents can be incorporated directly into the thermoplastic polymer during manufacture of the fibers. Suitable wetting agents for include non-ionic surfactants based on ethylene oxide-fatty alcohol ethers, ethoxylated adducts of propylene oxide with propylene glycol, fatty esters or sorbitol and glycerol, and the like.

The non-woven fabrics of the present invention generally have a basis weight in a range of from 25 grams per square meter (gsm) to 50 gsm, preferably in a range of from 30 gsm to 35 gsm and have a bulk (thickness) of between 10 to 20 mils, preferably from 12 to 16 mils.

The multi-denier non-woven fabrics of the present invention are particularly suitable for use as body-side liners in absorbent articles. In accordance with this embodiment of the present invention, there is provided a novel absorbent article having a body-facing fluid permeable cover sheet comprising a multi-denier non-woven fabric formed from an interconnected network thermoplastic polymer staple fibers, the fibers comprising a homogeneous blend of high denier fibers and low denier fibers having a denier in a range of from 2 denier to 15 denier, wherein the high denier fibers and the low denier fibers differ by at least one denier and wherein the high denier fibers are present in the blend in an amount of from 10 to 90% and the low denier fibers are present in the blend in an amount of from 90 to 10%.

The absorbent articles of this invention, include, but are not limited to disposable diapers, sanitary napkins, tampons, panty liners, and the like.

As is well known to those skilled in the art, absorbent articles which are worn externally, such as sanitary napkins, generally comprise a fluid impermeable backing sheet, an absorbent core, which is a layer of fluffy absorbent material positioned on the backing sheet, and a body side liner which is a non-woven fabric, formed from an open but interconnected network of oriented, thermoplastic staple fibers. During use, body side liner is in contact with or faces the user of the absorbent article. In accordance with this embodiment of the present invention, there is provided a novel absorbent article, such as a sanitary napkin, having a body-facing fluid permeable cover sheet, a garment-facing fluid impermeable barrier sheet, an absorbent core between the cover sheet and the barrier sheet, wherein the cover sheet is a multi-denier non-woven fabric formed from an interconnected network thermoplastic polymer fibers, the fibers comprising a homogeneous blend of high denier staple fibers and low denier staple fibers having a denier in a range of from 2 denier to 15 denier, wherein the high denier fibers and the low denier fibers differ by at least one denier and wherein the high denier fibers are present in the blend in an amount of from 10 to 90% and the low denier fibers are present in the blend in an amount of from 90 to 10%.

The body side liner and garment-facing fluid impermeable barrier sheet are usually substantially coextensive and are joined together about the periphery of the absorbent article by thermal fusion, adhesive, or in any other convenient manner. If desired, the absorbent core may be anchored to garment-facing fluid impermeable barrier sheet by one or more glue lines.

The fluid impermeable garment facing barrier layer may be of any flexible material that prevents the transfer through it of fluid but does not necessarily prevent the passages of gases. Commonly used materials are polyethylene or polypropylene films. Other materials that may be used as impermeable barriers may be chosen from films of polyesters, polyamides, polyethylene vinyl acetate, polyvinyl chloride, and polyvinylidene chloride. Co-extruded and laminated combinations of the foregoing, wherein such combinations are permitted by the chemical and physical properties of the film, may be used. Fluid impermeable nonreticulated foams and repellent treated papers may also be used. Films that are fluid barriers, but permit gases to transpire, i.e., "breathable films", may be used. These may be chosen from polyurethane films and from micro-porous films, where micro-porosity is created by ionizing radiation or by leaching out of soluble inclusions using aqueous or nonaqueous solvents. Fabrics whose surfaces have been made repellent or whose pores are small by virtue of close packing of fibers, or whose pores have been reduced in size by closing off large liquid admitting pores, may also be used alone, or together with breathable films, as breathable barriers. A suitable backing sheet material can be an opaque polyolefin, e.g., polyethylene, web impermeable to body fluids and about 0.001 inch thick. Another suitable sheet material for this purpose is a polyester, e.g., polyethylene terephthalate, web having a thickness of about 0.0005 inch.

The absorbent core can be a fluffy batt cut from a relatively loose web of non-woven fibers having a relatively high absorptive capacity. The absorbent core is usually of a rectangular configuration, and may optionally have inwardly curved side edges such as an hourglass shape. The absorbent core is somewhat smaller than the backing sheet and non-woven bodyside liner. The absorbent core may also be a fibrous batt having an integral densified layer. In such a case the absorbent core is positioned on the backing sheet of the absorbent article so that the densified layer adjoins the backing sheet. The densified layer has relatively higher wettability and liquid retentivity than the rest of the aforesaid batt and usually is formed by slightly moistening one surface of the batt and thereafter compressing the moistened surface.

The absorbent article may optionally comprise a multi-layered absorbent structure which may contain, in addition to the absorbent core, a transfer layer, which is a low density fluid accepting and fluid releasing layer, usually located between the absorbent core and the permeable body side liner. The transfer layer may be comprised of relatively less hydrophilic materials and structures, than is contained in the absorbent core, such as of webs of meltblown polypropylene or polyester fibers. Such webs may also contain woodpulp entrained within. Transfer layers may also be comprised of low density, highloft nonwoven webs comprised of woodpulp and synthetic fibers such as polyethylene, polypropylene, polyester, polyacrylonitrile and polyamide. Such highloft webs may be bonded with chemical binders or by thermal means such as by through-air bonding.

The thickness of the absorbent structure may be uniform throughout the expanse of the absorbent element or, for the purpose of specific fit, flexibility and absorbency requirements, the absorbent structure may be thicker in some regions than in others. For example, a particularly preferred thickness profile is an absorbent structure that is thicker in the central region than it is in the end regions.

The garment-facing fluid impermeable barrier sheet may be fixed or otherwise adhered to the surface of the absorbent structure overall or in discrete zones of attachment. The garment facing barrier layer may be adhered to the body side liner in an overlapping configuration for example parallel to the sides of the absorbent structure or parallel to the bottom of the absorbent article or in a flange seal extending from the sides of the absorbent structure. When the body side liner and garment facing barrier layer are adhered to each other in a flange seal, the body facing layer may additionally be wrapped around the flange seal about the body facing layer; or the garment facing layer may additionally be wrapped around the flange seal about the body facing layer.

The non-woven body side liner is readily permeable to body fluids and is made up of an open network of interconnected fiber elements which are a mixture low denier staple fibers, i.e., a mean denier not greater than about 4 and usually about 2 to about 4 and high denier staple fibers, i.e. a mean denier which is at least one denier higher than the low denier staple fibers and not greater than 15 and is usually about 4 to 6. A mean denier for the low denier staple fibers of about 2.5 to about 3.5 is preferred and a mean denier for the high denier fibers of about 4.5 to 5.5 is preferred. Additionally, some non-woven forming processes result in one surface of the non-woven fabric being softer than the opposite surface of the non-woven fabric. It is preferred that the softer fibrous outer surface be the body-facing surface when the non-woven fabric is incorporated into an absorbent article.

The thickness of the body side liner that is provided for the absorbent article of the present invention can vary, depending on the intended end use of the pads. Usually the body side liner is about 10 mil to about 20 mils thick. Body side liners produced in the foregoing manner usually have a good drape and hand, and a relatively smooth surface.

The absorbent articles of the present invention can be of various shapes and configurations depending on the intended end use, e.g., as disposable diapers, sanitary napkins, tampons, underpads, surgical dressings or wipes, and the like. Additionally, the present absorbent pads can be incorporated into a disposable or limited use garment as an integral part thereof. For example, an absorbent pad made according to the present invention can be a part of disposable training pants and similar garments.

The foregoing description is intended as illustrative and are not to be taken as limiting. Still other variations are possible without departing from the spirit and scope of this invention and will readily present themselves to one skilled in the art.

I claim:

1. An absorbant product comprising a body fluid-impermeable backing sheet, a layer of absorbent material on said backing sheet, and a soft, body fluid-permeable, body contacting, body side liner overlying said absorbent material; said body side liner being a non-woven fabric comprising an interconnected network thermoplastic polymer fibers, said fibers further comprising a homogeneous blend of high denier staple fibers and low denier staple fibers in a range of from 2 to 15 denier, wherein the high denier staple fibers and the low denier fibers staple differ by at least one denier and wherein the high denier staple fibers are present in the blend in an amount of from 10 to 90% and the low denier staple fibers are present in the blend in an amount of from 90 to 10%, wherein the high denier fibers have a denier in a range of from 4 to 15 and the low denier fibers have a denier in a range of from 2 to 4.

2. The absorbent product in accordance with claim 1 wherein the high denier staple fibers have a denier of 5 and the low denier staple fibers have a denier of 3.

3. The absorbent product in accordance with claim 1 wherein the fibers are polypropylene.

4. The absorbent product in accordance with claim 1 wherein the fabric has a basis weight of between 25 to 35 grams per square meter.

5. The absorbent product in accordance with claim 1 wherein the non-woven fabric the fibers contain titanium dioxide in an amount between 0.1% to 5%.

6. The absorbent product in accordance with claim 1 wherein the fibers contain titanium dioxide in an amount between 2% to 4%.

7. The absorbent product in accordance with claim 1 wherein the high denier fibers are in a range of from 30% to 70% and the low denier fibers are in a range of from 70% to 30%.

8. The absorbent product in accordance with claim 1 wherein the high denier fibers are in a range of from 40% to 60% and the low denier fibers are in a range of from 60% to 40%.

9. The absorbent product in accordance with claim 1 wherein the non-woven fabric is a carded web.

10. The absorbent product in accordance with claim 1 wherein a surface active agent is present on said fabric.

11. An absorbent product having a body contacting, body side liner and an underlying absorbent core wherein the body side liner comprises a multi-denier non-woven fabric formed from an interconnected network thermoplastic polymer fibers, said fibers further comprising a homogeneous blend of high denier fibers and low denier fibers in a range of from 2 to 15 denier, wherein the high denier fibers and the low denier fibers differ by at least one denier and wherein the high denier fibers are present in the blend in an amount of from 10 to 90% and the low denier fibers are present in the blend in an amount of from 90 to 10%, wherein the high denier fibers have a denier in a range of from 4 to 15 and the low denier fibers have a denier in a range of from 2 to 4.

12. The absorbent product in accordance with claim 11 wherein said absorbent product is a tampon.

13. The absorbent product in accordance with claim 11 wherein said absorbent product is a sanitary napkin.

14. The absorbent product in accordance with claim 11 wherein said fibers contain titanium dioxide in an amount from 1% to 5%.

15. The absorbent product in accordance with claim 11 wherein said fibers are made from a polyolefin.

16. The absorbent product in accordance with claim 11 wherein said fibers are made from polypropylene.

17. The absorbent product in accordance with claim 11 wherein a surface active agent is present on said body side liner.

18. The absorbent product in accordance with claim 17 wherein the surface active agent is hydrophilic.

* * * * *